United States Patent [19]

Walker

[11] Patent Number: 4,522,948
[45] Date of Patent: Jun. 11, 1985

[54] SPERMICIDAL SUBSTITUTED 1-(CYCLOALKYL)ALKYLIMIDAZOLES

[75] Inventor: Keith A. M. Walker, Los Altos Hills, Calif.

[73] Assignee: Syntex (U.S.A.) Inc., Palo Alto, Calif.

[21] Appl. No.: 256,877

[22] Filed: Apr. 24, 1981

[51] Int. Cl.³ .................. A61K 31/415; C07D 233/58
[52] U.S. Cl. ..................................... 514/396; 548/335
[58] Field of Search ..................... 548/335; 424/273 R

[56]  References Cited
U.S. PATENT DOCUMENTS 3,927,017  12/1975  Heeris et al. .......................... 548/335
4,284,641   8/1981  Thorogood .......................... 548/335

FOREIGN PATENT DOCUMENTS 2855329  7/1980  Fed. Rep. of Germany .

Primary Examiner—Richard A. Schwartz
Attorney, Agent, or Firm—Annette M. Moore; Tom M. Moran

[57]  ABSTRACT

New compounds of the formula

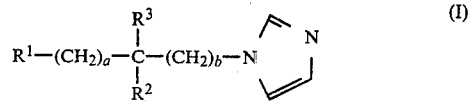

wherein:
$R^1$ is cycloalkyl of five to seven carbon atoms optionally substituted with one or more lower alkyl groups;
$R^2$ is alkyl of two to twelve carbon atoms, cycloalkyl of five to seven carbon atoms, or cycloalkylalkyl of six to ten carbon atoms wherein the cycloalkyl group may be optionally substituted with one or more lower alkyl groups;
$R^3$ is hydrogen or lower alkyl;
a is 0, 1, 2 or 3; and
b is 1, 2 or 3;

and the pharmaceutically acceptable acid addition salts thereof are useful as spermicidal and spermatostatic agents.

7 Claims, No Drawings

SPERMICIDAL SUBSTITUTED 1-(CYCLOALKYL)ALKYLIMIDAZOLES

BACKGROUND OF THE INVENTION

This invention concerns certain 1-substituted imidazoles which are useful as spermicidal and spermatostatic agents which are effective when administered either to male or female mammals.

Vast numbers of 1-substituted imidazole compounds are known. Various members of this group have been described as, for example, antifungals, antibacterials, antiprotozoals, anticonvulsants, food preservatives, crop disease protecting agents and CNS agents. U.S. Pat. No. 4,247,552, issued Jan. 27, 1981 and incorporated herein by reference discloses 1-substituted imidazoles which have spermicidal and spermatostatic activity.

It is known that compounds of the formula:

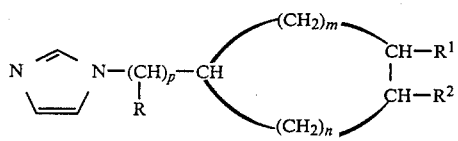

wherein R is, i.a., hydrogen or lower alkyl; $R^1$ and $R^2$ are hydrogen, lower alkyl or together may be a bond; the sum of m and n is zero to nine and p is zero to five: are useful for controlling cardiac infarct, thrombosis, ulcers, gastrointestinal acidity and as additives for blood. See German Pat. No. 2,855,329. A novel group of compounds which are useful as spermicidal and spermatostatic agents has now been prepared.

SUMMARY OF THE INVENTION

The first aspect of the present invention is a group of compounds of the formula

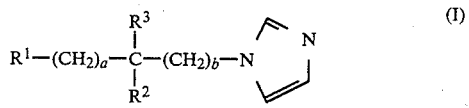

wherein:
- $R^1$ is cycloalkyl of five to seven carbon atoms optionally substituted with one or more lower alkyl groups;
- $R^2$ is alkyl of two to twelve carbon atoms, cycloalkyl of five to seven carbon atoms, or cycloalkylalkyl of six to ten carbon atoms wherein the cycloalkyl group may be optionally substituted with one or more lower alkyl groups;
- $R^3$ is hydrogen or lower alkyl;
- a is 0, 1, 2 or 3; and
- b is 1, 2 or 3;

and the pharmaceutically acceptable acid addition salts thereof.

Another aspect of the invention is compositions useful as spermatostatic or spermicidal agents comprising the compounds of the instant invention and a suitable carrier.

A further aspect of the invention is a method of contraception consisting of administering a compound of the present invention or a composition of the same to a female or male mammal.

Yet another aspect of the invention are processes for preparing a compound of Formula (I) above which comprises (1) reacting a compound of the formula

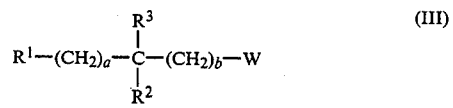

wherein $R^1$, $R^2$, $R^3$, a and b are as defined above and W is a leaving group, for example, halo (bromo, chloro or iodo) or a sulfonate ester such as methanesulfonate ester with imidazole and/or a metal salt, e.g., an alkali metal salt such as the sodium salt of imidazole, or (2) by hydrogenating the appropriately substituted 1-alkylimidazoles containing aromatic or olefinic unsaturation.

DETAILED DESCRIPTION AND PREFERRED EMBODIMENTS

As used in the specification and appended claims, unless specified to the contrary, the following terms have the meaning indicated.

"Alkyl" refers to a branched or unbranched saturated hydrocarbon substituent containing two to twelve carbon atoms, such as, for example, ethyl, i-propyl, n-butyl, n-hexyl, n-octyl or n-dodecyl.

"Lower alkyl" refers to a straight or branched chain monovalent substituent consisting solely of carbon and hydrogen containing no unsaturation and having one to four carbon atoms. Examples of lower alkyl are methyl, ethyl, i-propyl, n-propyl, n-butyl, i-butyl and t-butyl.

"Cycloalkyl" refers to a cyclic saturated monovalent substituent consisting solely of carbon and hydrogen and having five to seven carbon atoms in the ring. Examples of cycloalkyl are cyclopentyl, cyclohexyl and cycloheptyl.

"Cycloalkylalkyl" refers to a cycloalkyl group as defined above attached to an alkylene chain of one to three carbon atoms. Non-limiting Examples of cycloalkylalkyl groups are cyclopentylmethyl, cyclohexylethyl and cyclohexyl-n-propyl.

"Pharmaceutically acceptable acid addition salts" refers to those salts which possess the biological effectiveness and properties of the free bases and which are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, menthanesulfonic acid, ethanesulfonic acid, p-toluenesulfonic acid, salicylic acid and the like.

"Optional" or "optionally" means that the subsequently described event or circumstance may or may not occur, and that the description includes instances where said event or circumstance occurs and instances in which it does not. For example, "optionally substituted cycloalkyl" means that the cycloalkyl may or may not be substituted and that the description includes both unsubstituted cycloalkyl and cycloalkyl wherein there is substitution; "optionally followed by converting the free base to the acid addition salt" means that said conversion may or may not be carried out in order for the process described to fall within the invention, and the invention includes those processes wherein the free base is converted to the acid addition salt and those processes in which it is not.

"Spermatostatic" and "spermicidal" refer to the capacity to render spermatozoa ineffective. This effect may be the result of actual spermatozoon death, (spermicidal) or less drastically, immobility, cell membrane alteration or other impairment which results in the inability of the sperm cell to effect fertilization (spermatostatic).

Many of the compounds of the invention contain at least one chiral center, i.e., the carbon to which $R^3$ is attached.

Accordingly, many compounds of the present invention may be prepared in either optically active form, or as a racemic mixture. Unless otherwise specified, the compounds described herein are all in the racemic form. However, the scope of the subject invention herein is not to be considered limited to the racemic form, but to also encompass the individual optical isomers of the subject compounds.

If desired, racemic intermediates or final products prepared herein may be resolved into their optical antipodes by conventional resolution means known per se, for example, by the separation (e.g., fractional crystallization) of the diastereomeric compounds formed by reaction of racemic mixtures with optically resolved reactants.

Racemic compounds of Formula (I) and other basic intermediates may be resolved by reaction with optically active acids. Exemplary of such optically active acids are the optically active forms of camphor-10-sulfonic acid, α-bromocamphor-π-sulfonic acid, camphoric acid, menthoxyacetic acid, tartaric acid, malic acid, diacetyltartaric acid, pyrrolidone-5-carboxylic acid and the like.

Resolution of the enantiomers of the compounds of formula II (infra) is accomplished by separation of the diastereomeric esters or carbamates formed by reaction with optically active acids or isocyanates. Exemplary of such optically active isocyanates is α-(1-naphthyl)ethyl isocyanate, menthyl isocyanate and α-phenethyl isocyanate.

Carboxylic acid intermediates may also be resolved by a number of methods well known in the art, for example, through formation of and separation of their diastereomeric salts, formed by reaction with optically active amines, or esters formed with optically active alcohols. Typical of such amines and alcohols are, for example, the optically active forms of brucine, dehydroabietylamine, ephedrine, α-phenethylamine, 1-(1-naphthyl)ethylamine and menthol.

Under different conditions, the above mentioned amines may be used to form the corresponding amides.

The separated pure diastereomeric compounds described above may then be cleaved by standard means to afford the respective optical isomers of the racemic compound subjected to resolution.

Compounds of the present invention, or intermediates in the preparations thereof, described hereinbelow, may be isolated and purified by conventional means known in the art, such as fractional crystallization, extraction and solvent removal, high pressure liquid chromatography, column choromatography, thin layer chromatography and the like. The degree of purification required for any intermediate in the preparation sequences will, of course, depend on the nature of contaminants, and the selectivity of the subsequent reagents. The salt products are also isolated by conventional means. For example, the acidified reaction mixture containing the compound of Formula (I), may be evaporated to dryness, and the salts can be further purified by usual methods or the isolated free bases may be converted to an acid addition salt. Isolation of such salts is often more convenient, as many of the compounds of the invention, as free bases, are oils.

The compounds of formula (I) and the intermediates described hereinbelow are represented in expanded form elsewhere herein for ease of reading. Such representations are not intended to be Fischer projections, and no particular configuration should be inferred from these representations.

A preferred subgroup of compounds of formula (I) is that wherein $R^3$ is hydrogen or methyl.

A still more preferred subgroup is that wherein $R^2$ is alkyl of two to twelve carbon atoms (particularly straight chain alkyl when $R^2$ is alkyl of more than four carbon atoms), cycloalkyl of five to seven carbon atoms, or cycloalkylalkyl of six to ten carbon atoms wherein when a cycloalkyl group is cyclohexyl it is optionally substituted by one or more lower alkyl groups.

A still more preferred subgroups is that wherein $R^1$ is cycloalkyl of five to seven carbon atoms and when the cycloalkyl group is cyclohexyl, it is optionally substituted by one or more lower alkyl groups, but most preferably by only one alkyl group.

A still more preferred subgroup of compounds of formula (I) is that wherein $R^1$ is cyclohexyl optionally substituted by one or more lower alkyl groups. It is also preferred that when $R^2$ is cycloalkyl or cycloalkylalkyl that the cycloalkyl group is cyclohexyl optionally substituted by one or more lower alkyl groups.

A still more preferred subgroup is that wherein $R^1$ is cyclohexyl, $R^2$ is cyclohexyl, cyclohexylalkyl or alkyl of two to eight carbon atoms, preferably three to six carbon atoms, and when $R^2$ is alkyl of more than four carbon atoms, the alkyl group is straight chain alkyl and $R^3$ is hydrogen. A particularly preferred subgroup of the instant invention is that wherein b is 1. The most preferred subgroup is that wherein the compound of formula (I) is selected from the group consisting of:
1-[2-(cyclohexylmethyl)-n-pentyl]imidazole;
1-[2-(2-cyclohexylethyl)-n-pentyl]imidazole;
1-[2-(cyclohexylmethyl)-n-hexyl]imidazole;
1-[2-(2-cyclohexylethyl)-n-hexyl]imidazole;
1-[2-(cyclohexylmethyl)-n-heptyl]imidazole;
1-[2-(2-cyclohexylethyl)-n-heptyl]imidazole;
1-[2-(cyclohexylmethyl)-n-octyl]imidazole; and
1-[2-(2-cyclohexylethyl)-n-octyl]imidazole.

UTILITY AND ADMINISTRATION

The compounds of the instant invention and the pharmaceutically acceptable acid addition salts thereof are primarily useful as spermicidal or spermatostatic agents, either intravaginally administered to the female mammal or administered to the male mammals orally or by implant.

Compositions appropriate for such uses are prepared by methods and contain ingredients which are well known in the art. A generally recognized compendium of such methods and ingredients is *Remington's Pharmaceutical Sciences* by E. W. Martin, (Mark Publ. Co., 15th Ed., 1975).

For intravaginal administration suitable formulations are, for example, creams, gels, spray foams, suppositories and the like, as well as slow release materials. Each composition contains an effective amount of active ingredient plus one or more pharmaceutically acceptable excipients. Such excipients are, for example, starch, glucose, lactose, talc, cellulose and the like for solid formulations; polyethylene glycols, modified vegetable oils, mineral oil, or polyalkylene glycols and the like for semi-solid formulations; and water, alcohols, glycerol, lanolin, mineral oil and the like for liquid or semi-liquid compositions. The compositions may contain between about 0.01 and 10.0 percent by weight of the active ingredient, preferably between 0.05 and 2.0%, and may, if desired, contain other active ingredients. Such compositions may also be used in conjunction with barrier methods such as, e.g., diaphragms or condoms.

In the practice of the method of contraception herein, the above formulations are administered to the female before coitus, within a period of about 12 hours prior thereto. The preferred dosage range of active ingredient is from about 0.5 mg to 100 mg per vaginal administration for an adult human. For smaller mammals the amount would be correspondingly smaller.

Compositions for oral administration to the male will contain a spermicidal or spermatostatic amount of active ingredient with a non-toxic, pharmaceutically effective carrier. For oral administration solid dosage forms such as tablets, capsules and powders may contain such excipients as, for example, lactose, starch, or cellulose. Such compositions will contain the active ingredient in the range of about 0.2% to 99%, preferably from 50%–90%.

In the practice of the method of contraception herein, a dose in the range of between about 0.1 and 10 mg active ingredient per kg will be administered to the male prior to coitus, preferably at least 24 hours before coitus, and more preferably daily for 3–7 days prior to coitus.

The compounds of formula (I) and the acid addition salts thereof also have utility as antifungal, antibacterial and antiprotozoal agents.

PREPARATION

As mentioned above, compounds of Formula (I) may be prepared by reacting a compound of the formula

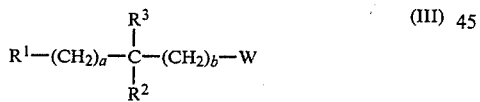

wherein $R^1$, $R^2$, $R^3$, a, b and W are as defined above with imidazole and/or a metal salt such as an alkali metal salt of imidazole. Compounds of Formula (III) are prepared from the corresponding alcohols of Formula (II).

The precursor alcohols of the formula

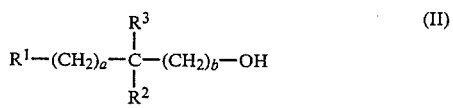

are prepared by one or more of the reaction sequences, described hereinbelow depending on the value of b.

The compounds of formula (II) wherein b is equal to 1, i.e., formula (II$_1$), below, are conveniently prepared by reduction of the corresponding carboxylic acids, which in turn, can be prepared by a number of methods known to those skilled in the art. These include, for example, malonic ester synthesis, alkylation of carboxylic acids or esters, and via the alkylation of β-keto esters, Meldrums acid, nitriles, or amides, and the like, preferably by malonic ester synthesis, optionally followed by alkylation of the resulting acid or ester. Exemplary of such a process is that shown in Reaction Sequence A:

Reaction Sequence A

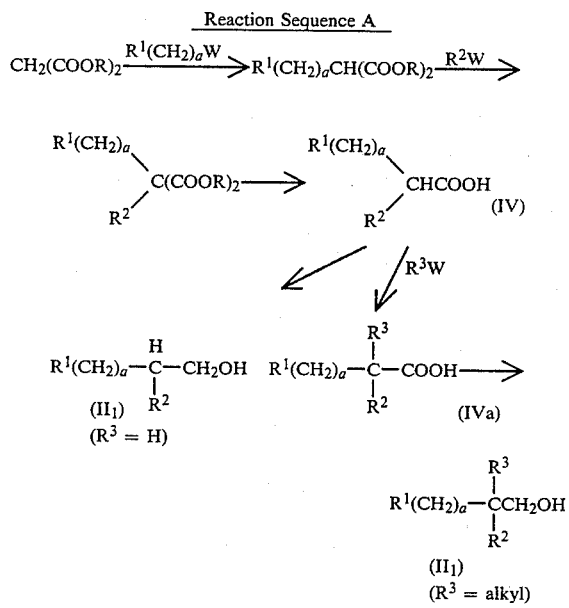

wherein R is a lower alkyl group, e.g., an ethyl group, and $R^1$, $R^2$, $R^3$, a and W are as defined above.

In the above sequence, the alkylation steps may, of course, be carried out in any order, and either $R^1(CH_2)_aW$, $R^2W$, or $R^3W$ may be added first. The conversion of the acid of formula (IV) to the acid of formula (IV$_a$) wherein $R^3$ is lower alkyl may be carried out as depicted by employing a dianion (e.g., the dilithium derivative) of the acid of formula (IV), or by alkylation of an ester derivative of the compound of formula (IV) (e.g., a t-butyl ester) with $R^3W$ followed by hydrolysis. The required reaction conditions for the malonic ester synthesis are well-known to those skilled in the art and are described, for example, in *Organic Chemistry* by Robert T. Morrison and Robert N. Boyd (2nd ed.) pp. 918–921 and the *Merck Index* (9th ed.) p. ONR-57.

The compound of formula (IV) or (IVa) is then reduced to the corresponding compound of formula (II) wherein b is 1, (II$_1$), using an appropriate reducing agent, such as, for example, borane-tetrahydrofuran complex or lithium aluminum hydride. The reducing agent, e.g., borane-tetrahydrofuran is added to a solution of the acid of formula (IV) or (IVa) in a solvent such as tetrahydrofuran at −20° to 30° C., preferably at −0° to 10° C. and stirred for 5 minutes to 1 hour, preferably for 15 minutes to 30 minutes and then allowed to warm to room temperature.

The intermediates of the formulas $R^1(CH_2)_aW$, $R^2W$ and $R^3W$ (wherein $R^3$ is lower alkyl) are commercially available, i.e. from Aldrich Chemical Co., or can be prepared by methods well known in the art. The hydroxy group of the corresponding alcohols may be converted to a suitable leaving group, W by the methods described hereinafter, or the above intermediates may be prepared by methods analogous to the methods depicted in reaction Sequence A or reaction Sequence B (infra). Another method of preparing compounds $R^1(CH_2)_aW$ or $R^2W$ is by hydrogenation of the analogous phenyl compound by, e.g. catalytic hydrogenation, discussed hereinafter.

Compounds of formula (II) wherein b is greater than 1, may be prepared by homologation of compounds of formula (II$_1$) or from its more highly oxidized cogeners. Exemplary of such homologations is the sequence depicted in Reaction Sequence B:

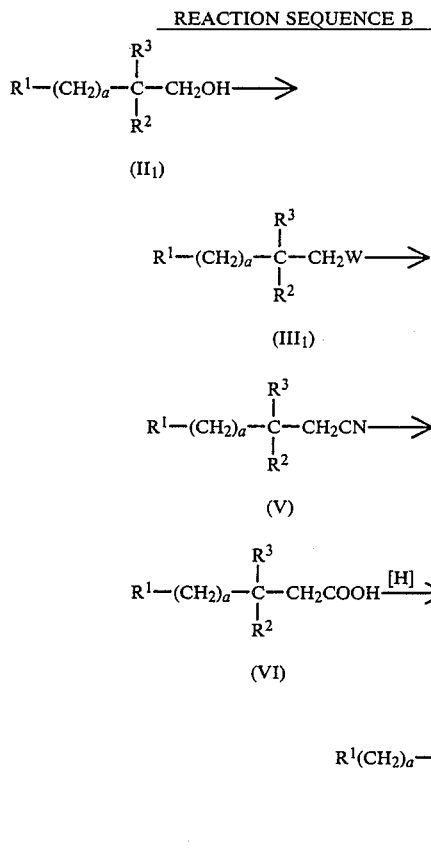

wherein in compound of formula (III$_1$) b is 1 and in compound (II$_2$) b is 2.

In the above sequence, the halide or sulfonate of formula (III$_1$) (b is 1) is converted to the nitrile of formula (V) by reaction with, for example, sodium cyanide in dimethylformamide. The mixture is heated to 50° to 100° C., preferably to 60° to 90° C. for 1 to 24 hours, preferably overnight. The nitrile derivative is hydrolyzed by heating the reaction mixture to reflux for 1 to 24 hours, preferably overnight in the presence of a strong acid, e.g., aqueous sulfuric acid. Reduction as described above in Reaction Sequence A gives the alcohol of formula (II$_2$). Reaction Sequence B, can, of course, be repeated, resulting in a compound of formula II wherein b is 3 (II$_3$).

Similarly, the acid of formula (IV) or (IVa) (Reaction Sequence A) may be homologated to the acid of formula (VI) by methods well known to those skilled in the art, for example, using the Arndt-Eistert reaction or the Wolff Rearrangement as described in, for example, Merck Index (9th ed.) p. ONR-5 and pp. ONR-95-ONR-96. Again the resulting acid is reduced to the compound of formula (II$_2$) which can, of course, then be resub-jected to Reaction Sequence B to yield the compound of formula (II$_3$).

Another method for the preparation of certain alcohols of formula (II) wherein b is 2 is depicted in Reaction Sequence C:

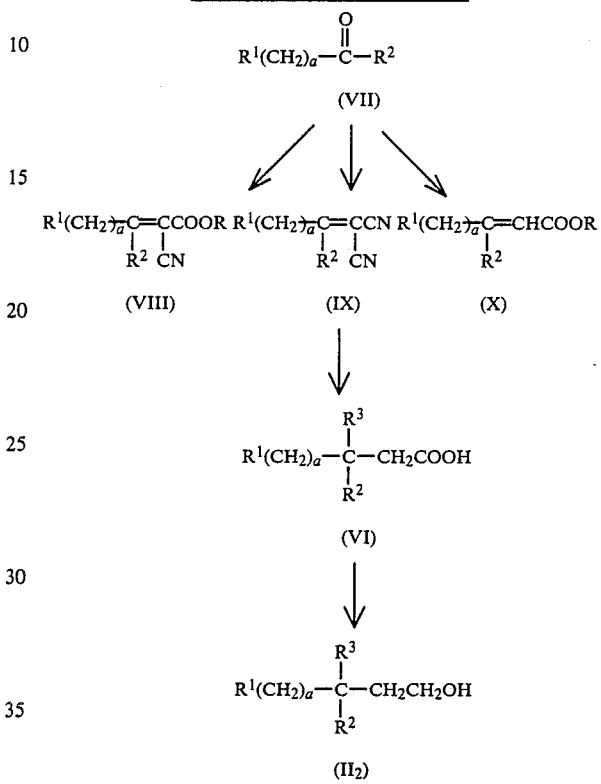

wherein R is a lower alkyl group, e.g. ethyl or t-butyl.

In the above Sequence, a ketone of formula (VII) is converted to an olefin of formula (VIII), (IX) or (X) by methods well known in the art. For example, condensation with cyanoacetic ester or malononitrile gives the compounds of formulas (VIII) and (IX) respectively; whereas the compound of formula (X) is obtained, for example, by Wittig (Horner-Emmons) olefination as described in, for example, Merck Index (9th ed.) p. ONR-94 and using a phosphorane (or phosphonate anion) or using a trialkylsilylacetic ester derivative. The respective compounds of formulas (VIII), (IX) and (X) are then converted by conventional means, to the acid of formula (VI), wherein $R^3$ is hydrogen. Alternatively, treatment of the compound of formula (VIII) with a dialkylcopper lithium reagent, or compound of formula (IX) with an alkyl Grignard Reagent, followed by hydrolysis and pyrolysis, is productive of the acid of formula (VI) wherein $R^3$ is lower alkyl.

The ketones of formula (VII) insofar as they may not be known or be commercially available may be prepared by various methods well known in the art, for example by alkylation of a dithiane derivative and hydrolysis.

Yet another preparation of compounds of formula (II), wherein b is 2 is depicted in Reaction Sequence D.

REACTION SEQUENCE D

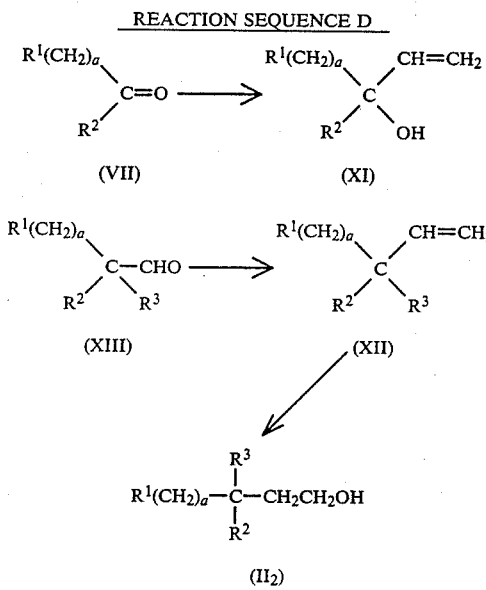

In the above Sequence, a vinyl carbinol of formula (XI) is prepared by standard methods, e.g., from the ketone of formula (VII) and vinyl lithium or a vinyl magnesium halide (or, by addition of a $R^1(CH_2)_a$- or $R^2$- derivative to the appropriate vinyl ketone), and is converted to a compound of formula (XII) wherein $R^3$ is methyl by reaction with methyl lithium in the presence of a palladium complex as described in *J. Amer. Chem. Soc.* 1978, 100, 6445. Alternatively, Wittig olefination of the aldehyde of formula (XIII) is productive of the olefin of formula (XII). Standard hydroboration and oxidation procedures yield an alcohol of formula ($II_2$). The aldehydes of formula (XIII) may be prepared by a number of methods well known in the art, for example, by the alkylation of an aldehyde or aldehyde derivative, especially an enamine derivative, or by reduction (e.g., using diisobutylaluminum hydride) of the corresponding nitriles which may also be used as intermediates in the preparation of the acids of formula (IV) or (IVa) of Reaction Sequence A.

Compounds of formula (II) wherein b is 3, formula ($II_3$), may be prepared as depicted in Reaction Sequence E:

REACTION SEQUENCE E

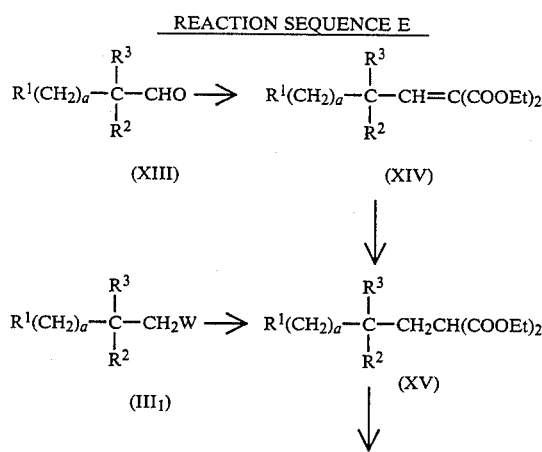

-continued
REACTION SEQUENCE E

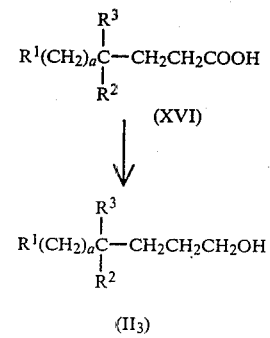

where a, W, $R^1$, $R^2$ and $R^3$ are as defined above.

In the above Sequence, the halide of sulphonate of formula ($III_1$) is converted to the malonic ester of formula (XV) and then to the acid of formula (XVI) in a similar manner as that described in Reaction Sequence A.

Alternatively, the aldehyde of formula (XIII) is condensed to give the olefin of formula (XIV) (Knoevenagel Reaction as described in, for example, the *Merck Index*, (9th ed.) pp. ONR-50 to ONR-51). Reduction by conventional means is productive of the ester of formula (XV). Reduction of the acid of formula (XVI) by the methods described above in Reaction Sequence A gives the alcohol of formula ($II_3$).

The compounds of formula (I) are prepared by reacting the compounds of formula (III) with imidazole and-/or a metal salt e.g. an alkali metal salt such as a sodium salt thereof.

Certain compounds of formula (II) may also be obtained by reduction (e.g., with sodium borohydride) of an aldehyde of formula (XIII) (supra). Aldehydes of formula (XIII) may be prepared by methods well known in the art, e.g., by alkylation of an aldehyde or aldehyde derivative, especially an enamine derivative.

The conversion of compounds of formula (II) to compounds of formula (III) may be accomplished by treating a compound of formula (II) with either a halogenating agent, such as, for example, thionyl bromide or N-bromosuccinimide/triphenylphosphine or with an appropriate sulfonyl halide, for example, a sulfonyl chloride, optionally in an inert solvent, such as, for example, dichloromethane, or tetrahydrofuran in the presence of a base, for example, a tertiary amine, such as, for example, pyridine or triethylamine. The base may also be used as the solvent, for example, pyridine. The reaction is carried out at a temperature of about −20° C. to about 50° C., preferably 0° C. to 25° C. and over a period of 5 minutes to 24 hours preferably, 30 minutes to overnight. Thereafter, the compound of formula (III) is converted to the final product of formula (I), by treating compound of formula (III) with at least one mole of imidazole per mole of compound of formula (III), preferably an excess (e.g. 1.1 to 5 moles imidazole per mole of compound of formula (III)). The reaction takes place in the absence of solvent (above the melting point of the mixture) or in an inert organic solvent such as dimethylformamide (DMF), acetonitrile, tetrahydrofuran, dimethylsulfoxide (DMSO) and the like; preferably, dimethylformamide, at a temperature between about 0° to 170° C., most preferably from about 50° to 150° C. Alternatively, the reaction may be carried out using a salt of imidazole, for example, an alkali metal salt, preferably a sodium salt, in the same solvents, at a temperature from about 0° to 150° C., preferably from about 20° to about 110° C.

Another method for preparing the compounds of Formula (I) wherein $R^3$ is hydrogen is depicted in Reaction Sequence F.

of formulas (XVII) and (XVIII), respectively by Wittig olefination. The ketones of formulas (XVII) and (XVIII) may be prepared by the general methods described in U.S. Pat. No. 4,059,705.

The compound of formula (I) may also be prepared by catalytically hydrogenating the precursor phenyl imidazole compound wherein the phenyl ring is option-

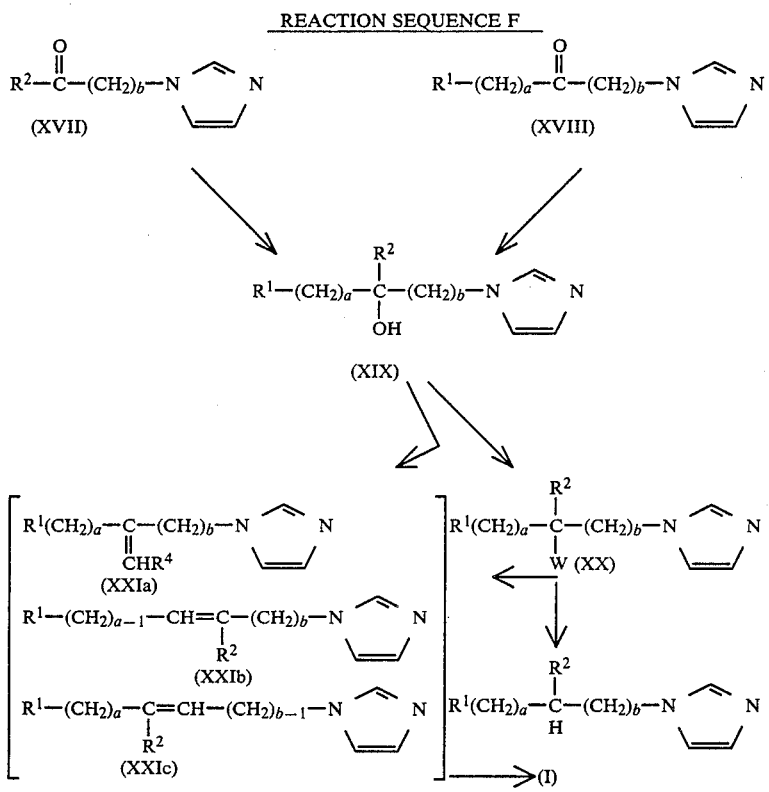

REACTION SEQUENCE F wherein $R^1$, $R^2$, W, a and b are as defined above and $R^4$ is alkyl of one to eleven carbon atoms, cycloalkyl of five to seven carbon atoms or cycloalkylalkyl with an alkylene group of one to two carbon atoms.

In the above Sequence, the imidazole ketones of formula (XVII) or (XVIII) are converted to the imidazole alcohol of formula (XIX) by reaction with an organometallic reagent, such as $R^2M$ or $R^1(CH_2)_aM$, respectively, wherein M equals, for example, —Li or —MgX wherein X is halo, e.g. chloro or bromo. The alcohol of formula (XIX) is then converted to a compound of Formula (XX) wherein W is a leaving group, e.g. halo or a sulfonate ester. Elimination of W from the compounds of formula (XX) e.g. using base, or dehydration of the alcohol of formula (XIX) by standard methods is productive of one or more of the olefins of formulas (XXI) (a, b or c). Hydrogenation of the compound(s) of formula (XXI), e.g., using a noble metal catalyst and hydrogen gas or via ionic hydrogenation produces the respective compounds of formula (I). When catalytic hydrogenation is used, it may be necessary to pretreat the solution of olefins of formula (XXI) with catalyst to remove catalytic poisons. Alternatively, the respective compounds of formula (I) wherein $R^3$ is hydrogen may be obtained by reduction (e.g., by catalytic hydrogenation or chemically, for example, by using lithium aluminum hydride) of the compounds of formula (XX). In addition to the method depicted in Reaction Sequence F the olefins of formulas (XXIb) and (XXIa) (or isomers thereof) may also be directly prepared from the ketones ally substituted by lower alkyl. The precursor compound, dissolved in an inert solvent, is hydrogenated using a catalyst such as rhodium on alumina at a pressure of about three to four atmospheres and a temperature of about 60° to 80° C. The precursor phenyl imidazole compounds are prepared by the methods analogous to those discussed for the preparation of the novel compounds herein.

The following examples are illustrative of the methods and compositions of the present invention. They should not be construed as limitative thereof in any manner.

PREPARATION I

This preparation illustrates the process of preparing compounds of Formula (II$_1$) in reaction Sequence A wherein $R^3$ is hydrogen, a is 1, b is 1, $R^1$ is cyclohexyl and $R^2$ is n-butyl.

(A) Diethyl malonate (16.0 g) was added to a freshly prepared solution of sodium ethoxide (from 2.3 g of sodium in 150 ml of absolute ethanol), followed by 17.7 g of cyclohexylmethyl bromide. The mixture was heated under reflux for four hours and evaporated to dryness. The resulting mixture was treated with water, extracted with ethyl acetate and the extracts washed with water, brine and dried (MgSO$_4$). Evaporation gave an oil which was distilled in vacuo to give 17 g of diethyl(cyclohexylmethyl)malonate (b.p. 104°–107° C. at 0.2 mm Hg).

(B) Diethyl(cyclohexylmethyl)malonate (5.12 g) was added to a solution of sodium ethoxide (from 0.5 g of sodium in ethanol (50 ml)) and the mixture warmed to 60° C. n-Butyl bromide (4.0 g) was then added and the mixture heated overnight under reflux, and the crude product isolated as in Part A above. Chromatography on silica gel eluting with 0–7.5% ethyl acetate in hexane gave pure diethyl 2-n-butyl-2-(cyclohexylmethyl)malonate.

(C) A mixture of diethyl 2-n-butyl-2-(cyclohexylmethyl)malonate (1.8 g) and potassium hydroxide (10 g) in water (10 ml) and methanol (10 ml) were heated under reflux for 4 hours. The methanol was evaporated under reduced pressure and the residue treated with water (50 ml), cooled to 0° C., and acidified with concentrated hydrochloric acid. The product was extracted with ethyl acetate and the extracts washed with brine, dried (MgSO$_4$) and evaporated to give 2-n-butyl-2-(cyclohexylmethyl)malonic acid. Without further purification the acid was heated to about 160° until the evolution of carbon dioxide ceased, and cooled to give 2-(cyclohexylmethyl)hexanoic acid.

(D) A solution of 2-(cyclohexylmethyl)hexanoic acid (1.4 g) in 50 ml of dry tetrahydrofuran at 0° C. under nitrogen was treated with stirring with 10 ml of 1 molar borane-tetrahydrofuran complex. The mixture was stirred for 30 minutes, allowed to come to room temperature, and poured into ethyl acetate. After careful addition of water, the organic layer was separated, washed with brine, dried (MgSO$_4$) and evaporated to give 1.4 g of 2-(cyclohexylmethyl)hexan-1-ol.

(E) Similarly, proceeding as above, substituting the appropriate cycloalkyl or cycloalkylalkyl bromide in Part (A) For cyclohexylmethylbromide and substituting the appropriate alkyl, cycloalkyl or cycloalkylalkylbromide in Part (B) for n-butylbromide, the following compounds are prepared:

2-(cyclohexylmethyl)butan-1-ol;
2-(cyclohexylmethyl)-3-methylbutan-1-ol;
2-(cyclohexylmethyl)-3,3-dimethylbutan-1-ol;
2-(cyclohexylmethyl)-pentan-1-ol;
2-(cyclohexylmethyl)-4-methylpentan-1-ol;
2-(cyclohexylmethyl)-heptan-1-ol;
2-(cyclohexylmethyl)-octan-1-ol;
2-(cyclohexylmethyl)-decan-1-ol;
2-(cyclohexylmethyl)-dodecan-1-ol;
2-(cyclohexylmethyl)-tetradecan-1-ol;
2,3-(dicyclohexyl)propan-1-ol;
3-cyclohexyl-2-cyclohexylmethylpropan-1-ol;
(2-cyclopentylmethyl-3-cyclopentyl)propan-1-ol;
(2-cycloheptylmethyl-3-cycloheptyl)propan-1-ol;
2-(cyclohexyl)hexan-1-ol;
2-(cycloheptyl)hexan-1-ol;
2-(4-methylcyclohexyl)hexan-1-ol;
21-(cyclopentylmethyl)hexan-1-ol;
2-(cycloheptylmethyl)hexan-1-ol;
2-[2-(cyclopentyl)ethyl]hexan-1-ol;
2-[2-(cyclohexyl)ethyl]pentan-1-ol;
2-[2-(cyclohexyl)ethyl]hexan-1-ol;
2-[3-(cyclopentyl)propyl]hexan-1-ol;
2-[3-(cyclohexyl)propyl]pentan-1-ol;
2-[3-(cyclohexyl)propyl]hexan-1-ol;
2-(2-methylcyclohexylmethyl)hexan-1-ol;
2-(4-methylcyclohexylmethyl)hexan-1-ol;
2-(4-i-propylcyclohexylmethyl)hexan-1-ol;
2-(4-t-butylcyclohexylmethyl)hexan-1-ol; and
2-[2-(cyclohexyl)ethyl]octan-1-ol.

PREPARATION II

This preparation illustrates the process in reaction Sequence B for preparing compound of formula (II$_2$) wherein b is 2, a is 1, R$^1$ is cyclohexyl and R2 is n-butyl.

(A) 2-(Cyclohexylmethyl)hexyl methanesulfonate (2.0 g) in a few ml of dimethylformamide (DMF) was added to a cooled stirred suspension of anhydrous sodium cyanide (0.53 g) in 5 ml of dry DMF. The mixture was heated overnight at 80° C., poured into water (100 ml) and the product extracted with ether. The combined extracts were washed with water, dried (MgSO$_4$) and evaporated to give 3-(cyclohexylmethyl)heptanenitrile, used directly in the next step.

(B) 3-(Cyclohexylmethyl)heptanenitrile (1.43 g) in 10 ml of 50% aqueous sulfuric acid was heated under reflux overnight. The cooled mixture was then poured into water (100 ml) and extracted twice with ether. The ethereal extracts were washed with water, dried (MgSO$_4$) and evaporated to give 3-(cyclohexylmethyl)heptanoic acid.

(C) 3-(Cyclohexylmethyl)heptanoic acid was converted to 3-(cyclohexylmethyl)heptan-1-ol by the method described in Preparation I, Part D.

(D) Similarly, proceeding as above, substituting the appropriate methanesulfonate for 2-(cyclohexylmethyl)hexyl methanesulfonate the following compounds are prepared:

3-(cyclohexylmethyl)pentan-1-ol;
3-(cyclohexylmethyl)hexan-1-ol;
3-(2-methylcyclohexylmethyl)hexan-1-ol;
3-(4-methylcyclohexylmethyl)hexan-1-ol;
3-(cyclohexylmethyl)heptan-1-ol;
3-[2-(cyclohexyl)ethyl]pentan-1-ol;
3-[2-(cyclohexyl)ethyl]hexan-1-ol;
3-[2-(cyclohexyl)ethyl]heptan-1-ol;
3-(cyclohexylmethyl)-3-(cyclohexyl)propan-1-ol;
3-(cyclopentylmethyl)hexan-1-ol;
3-(cycloheptylmethyl)hexan-1-ol;
3-(cyclohexyl)pentan-1-ol;
3-(cyclohexyl)hexan-1-ol; and
3-(cyclohexyl)heptan-1-ol.

PREPARATION III

This preparation illustrates the process in reaction Sequence B for preparing compounds of formula (II$_3$) wherein b is 3, a is 1, R$^1$ is cyclohexyl and R$^2$ is n-butyl.

Following the procedure of Preparation II 3-(cyclohexylmethyl)heptan-1-ol is converted to 3-(cyclohexylmethyl)heptyl methanesulfonate which in turn is converted to 4-(cyclohexylmethyl) octanenitrile. The nitrile is hydrolyzed to 4-(cyclohexylmethyl)octanoic acid which is reduced to 4-(cyclohexylmethyl)octan-1-ol.

Similarly, proceeding as above, substituting the appropriate alcohol for 3-(cyclohexylmethyl)heptan-1-ol, the following compounds are prepared:

4-(cyclohexylmethyl)heptan-1-ol;
4-(cyclohexyl)heptan-1-ol;
4-(cyclopentylmethyl)heptan-1-ol; and
4-(cyclohexyl)octan-1-ol.

PREPARATION IV

This preparation illustrates the process of reaction Sequence A for preparing compounds of formula (II) wherein R$^3$ is methyl, a is 1, b is 1, R$^1$ is cyclohexyl and R$^2$ is n-butyl.

A mixture of 45 ml of dry tetrahydrofuran and diisopropylamine (6.1 g) was purged with nitrogen and cooled to −20° C., whereupon a 1.5M solution of n-butyllithium in hexane (40 ml) was added with stirring such that the temperature did not exceed 0° C. 2-(Cyclohexylmethyl)hexanoic acid (5.83 g) from Preparation I in a few ml of dry tetrahydrofuran was then added, maintaining the temperature below 0° C., and the resulting mixture stirred at 50° C. for 2 hours, and cooled again to 0° C. Methyl iodide (4.26 g) was added in one portion to the mixture and the reaction allowed to come to room temperature for two hours, before evaporation of the solvent. The residue was acidified with ice cold 10% hydrochloric acid and the product extracted twice with ether. The combined extracts were washed with dilute hydrochloric acid, water, dried (MgSO$_4$) and evaporated to give 2-(cyclohexylmethyl)-2-methylhexanoic acid, which was reduced to the alcohol without further purification as described in Preparation I, Part D to give 2-cyclohexylmethyl-2-methylhexan-1-ol. Similarly, proceeding as above, substituting the appropriate alkyllithium for n-butyllithium and the appropriate carboxylic acid for 2-(cyclohexylmethyl)hexanoic acid, the following compounds are prepared.

2-(cyclohexylmethyl)-2-methylpentan-1-ol;
2-(cyclohexylmethyl)-2-methylhexan-1-ol;
2-(cyclohexylmethyl)-2-n-butylhexan-1-ol; and
3-(cyclohexylmethyl)-3-methylpentan-1-ol.

EXAMPLE 1

This example illustrates the preparation of compound of formula (I) where $R^1$ is cyclohexyl, $R^2$ is n-butyl, $R^3$ is hydrogen, a is 1 and b is 1.

(A) A solution of 2-(cyclohexylmethyl)hexan-1-ol (1.3 g) in 10 ml of dry pyridine under nitrogen was cooled to 0° C. and treated dropwise with stirring with 1.0 g of methanesulfonyl chloride. After 1 hour the mixture was poured into water and extracted with ethyl acetate. The extracts were washed twice with dilute hydrochloric acid, once with brine and dried (MgSO$_4$). Evaporation of the solvent gave an oil, 2-(cyclohexylmethyl)hex-1-yl methanesulfonate, which was used directly in the next step.

(B) The above oil was added to a mixture of 3.0 g of imidazole in 5 ml of dimethyl formamide and the mixture heated at 130° C. for one hour under nitrogen. The reaction mixture was then poured into ethyl acetate, and the organic layer washed four times with water, and dried (MgSO$_4$). Evaporation of the ethyl acetate gave an oil which was purified by chromatography on silica gel eluting with 0-5% methanol in dichloromethane. The product, 1-[2-(cyclohexylmethyl)-n-hexyl]imidazole was obtained as an oil (1.2 g).

(C) Treatment of the free base in ether with sulfuric acid dropwise until precipitation was complete gave the hydrogen sulfate salt, which was collected and recrystallized from ethyl acetate to give 1-[2-(cyclohexylmethyl)-n-hexyl]imidazole hydrogen sulfate, m.p. 152° C. (gels), 190°-192° C. final melt.

(D) Similarly, proceeding as above, substituting the appropriate alcohol in Part A for 2-(cyclohexylmethyl)hexan-1-ol, the following compounds are prepared which may be further characterized as the acid addition salts indicated:

1-[2-(cyclohexylmethyl)-n-butyl]imidazole;
1-[2-(cyclohexylmethyl)-3-methylbutyl]imidazole;
1-[2-(cyclohexylmethyl)-3,3-dimethylbutyl]imidazole;
1-[2-(cyclohexylmethyl)-n-pentyl]imidazole;
1-[2-(cyclohexylmethyl)-4-methylpentyl]imidazole;
1-[2-(cyclohexylmethyl)-n-hexyl]imidazole, hydrogen oxalate salt, m.p. 119°-120° C.;
1-[2-(cyclohexylmethyl)-n-heptyl]imidazole;
-[2-(cyclohexylmethyl)-n-octyl]imidazole, hydrogen oxalate salt, m.p. 105°-106° C.;
1-[2-(cyclohexylmethyl)-n-decyl]imidazole;
1-[2-(cyclohexylmethyl)-n-dodecyl]imidazole;
1-[2-(cyclohexylmethyl)-n-tetradecyl]imidazole;
1-[2,3-dicyclohexyl-n-propyl]imidazole;
1-[3-cyclohexyl-2-(cyclohexylmethyl)-n-propyl]imidazole;
1-[2-cyclopentylmethyl-3-cyclopentyl-n-propyl]imidazole;
1-[2-cycloheptylmethyl-3-cycloheptyl-n-propyl]imidazole;
1-[2-(cyclohexyl)-n-hexyl]imidazole hydrogen oxalate salt, m.p. 122°-124° C.;
1-[2-cycloheptyl-n-hexyl]imidazole;
1-[2-(4-methylcyclohexyl)-n-hexyl]imidazole;
1-[2-(cyclopentylmethyl)-n-hexyl]imidazole;
1-[2-(cycloheptylmethyl)-n-hexyl]imidazole;
1-[2-(2-cyclopentylethyl)-n-hexyl]imidazole;
1-[2-(2-cyclohexylethyl)-n-pentyl]imidazole;
1-[2-(2-cyclohexylethyl)-n-hexyl]imidazole;
1-[2-(3-cyclopentylpropyl)-n-hexyl]imidazole;
1-[2-(3-cyclohexylpropyl)-n-pentyl]imidazole;
1-[2-(3-cyclohexylpropyl)-n-hexyl]imidazole;
1-[2-(2-methylcyclohexylmethyl)-n-hexyl]imidazole;
1-[2-(4-methylcyclohexylmethyl)-n-hexyl]imidazole;
1-[2-(4-i-propylcyclohexylmethyl)-n-hexyl]imidazole;
1-[2-(4-t-butylcyclohexylmethyl)-n-hexyl]imidazole;
1-[2-(2-cyclohexylethyl)-n-octyl]imidazole, hydrogen oxalate salt, m.p. 124°-125° C.;
1-[3-(cyclohexylmethyl)-n-pentyl]imidazole;
1-[3-(cyclohexylmethyl)-n-hexyl]imidazole;
1-[3-(2-methylcyclohexylmethyl)-n-hexyl]imidazole;
1-[3-(4-methylcyclohexylmethyl)-n-hexyl]imidazole;
1-[3-(cyclohexylmethyl)-n-heptyl]imidazole;
1-[3-(2-cyclohexylethyl)-n-pentyl]imidazole;
1-[3-(2-cyclohexylethyl)-n-hexyl]imidazole, hydrogen oxalate salt, m.p. 75°-77° C.;
1-[3-(2-cyclohexylethyl)-n-heptyl]imidazole;
1-[3,4-dicyclohexyl-n-butyl]imidazole;
1-[3-(cyclopentylmethyl)-n-hexyl]imidazole;
1-[3-(cycloheptylmethyl)-n-hexyl]imidazole;
1-[3-(cyclohexyl)-n-pentyl]imidazole;
1-[3-(cyclohexyl)-n-hexyl]imidazole;
1-[3-(cyclohexyl)-n-heptyl]imidazole;
1-[4-(cyclohexylmethyl)-n-heptyl]imidazole;
1-[4-(cyclohexyl)-n-heptyl]imidazole;
1-[4-(cyclopentylmethyl)-n-heptyl]imidazole;
1-[4-cyclohexyl-n-octyl]imidazole;
1-[2-(cyclohexylmethyl)-2-methylpentyl]imidazole;
1-[2-(cyclohexylmethyl)-2-methylhexyl]imidazole;
1-[2-(cyclohexylmethyl)-2-n-butylhexyl]imidazole; and
1-[3-(cyclohexylmethyl)-3-methylpentyl]imidazole.

EXAMPLE 2

This example illustrates the process in reaction Sequence F for preparing compounds of formula (I) where $R^1$ is cyclohexyl, $R^2$ is n-butyl, $R^3$ is hydrogen, a is 1 and b is 2.

1-[4-Cyclohexyl-2-oxo-n-butyl]imidazole (2.2 g) in 15 ml of dry tetrahydrofuran was added dropwise to a stirred solution of butylmagnesium bromide [from butyl bromide (2.05 g) and magnesium (0.36 g)]in 20 ml of tetrahydrofuran at 0° C. under nitrogen. After one hour the mixture was allowed to come to room temperature and quenched with saturated ammonium chloride. Most of the tetrahydrofuran was removed under reduced pressure and the residue treated with aqueous potassium carbonate and extracted with ethyl acetate. The extracts were washed, dried (MgSO₄) and evaporated to give 1-[3-(cyclohexylmethyl)-3-hydroxy-n-heptyl]imidazole. Purification could be effected if needed by chromatographpy on silica gel eluting with 5% methanol in methylene chloride.

The above alcohol (1.5 g) in pyridine (15 ml) was treated dropwise with stirring at 0° C. with 3 ml of thionyl chloride. The mixture was stirred for 4 hours at 0° C. and allowed to come to room temperature overnight. The pyridine was removed in vacuo and the residue treated with aqueous potassium carbonate and extracted with ether. The extracts were washed with water, dried (MgSO₄) and evaporated to give 1-[3-(cyclohexylmethyl)hept-3-enyl]imidazole and isomeric olefins, used directly in the next step.

The mixture of olefins from above (1.0 g) in ethanol containing 10% acetic acid (20 ml) was hydrogenated at ambient temperature and pressure over 10% palladium on charcoal (100 mg). When the uptake of hydrogen ceased, the solution was filtered and evaporated to give 1-[3-(cyclohexylmethyl)-n-heptyl]imidazole as an oil.

This oil in ether (30 ml) was treated dropwise with ethereal oxalic acid until precipitation was complete, whereupon the precipitate was collected and recrystallized from ethyl acetate to give the hydrogen oxalate salt of 1-[3-(cyclohexylmethyl)-n-heptyl]imidazole.

EXAMPLE 3

1.2 g of 1-[2-(cyclohexylmethyl)-n-hexyl]imidazole, as an oil, was dissolved in ether (50 ml). Sulfuric acid was added dropwise until precipitation was complete. The hydrogen sulfate salt was collected and recrystallized from ethyl acetate to give 1-[2-cyclohexylmethyl-n-hexyl]imidazole hydrogen sulfate, m.p. 152° C. (gels), 190°–192° C. final melt.

In a similar manner, all compounds of Formula (I) in base form can be converted to their acid addition salt by treatment with the appropriate acid, for example, those acids set out herein above.

EXAMPLE 4

A mixture of 1.0 g of 1-[2-(cyclohexylmethyl)-n-hexyl]imidazole hydrogen sulfate, ether (50 ml) and excess aqueous potassium carbonate was stirred until no solid remained. The ether layer was separated, washed with water, dried (MgSO₄) and evaporated to give 1-[2-(cyclohexylmethyl)-n-hexyl]imidazole as an oil.

In a similar manner, all compounds of the present invention, as their acid addition salts may be converted to the corresponding compounds of Formula I in base form.

EXAMPLE 5

The following illustrates formulations for vaginal administration in contraceptive uses of the compounds of the present invention. The specific active ingredient utilized is 1-[2-(cyclohexylmethyl)-n-hexyl]imidazole; as the hydrogen sulfate salt although any compound of the invention may be utilized.

(a) Water soluble vaginal cream

| Ingredients | % w/w |
|---|---|
| Active ingredient | 1.0 |
| Cetostearyl alcohol | 12.0 |
| Polysorbate 60 | 2.0 |
| Sorbitan monostearate | 2.0 |
| Mineral oil | 2.0 |
| Propylene glycol | 4.0 |
| Benzyl alcohol | 1.0 |
| Butylated hydroxyanisole | 0.01 |
| Purified water qs ad | 100.0 |

All ingredients except the active ingredient, water, and 10% of the Polysorbate 60 are mixed and heated to 70°–80°. 85% of the required water is separately heated to 70°–80°. The remaining Polysorbate 60 and 10% of the water are dissolved together at 50°–60°, and the active ingredient dissolved therein.

The heated water is then added to the heated emulsifying ingredients using a homomixer at medium speed, with a final increase to high speed for 1 minute after mixing is complete. The homomixer is removed and mixing continued gently until the mixture congeals and cools to room temperature; whereupon the active ingredient, previously dissolved as described above, is added, and gentle mixing continued for 20–30 minutes. The remaining 5% of water is then used to rinse the vessels containing the premixed active ingredient and the rinse added to the total mixture. Mixing is continued and further water added if necessary.

For each application approximately 1 gm of the cream is vaginally administered to an adult human female with a suitable syringe.

(b) Vaginal jelly

| Ingredients | % w/w |
|---|---|
| Active ingredient | 1.00 |
| Tragacanth | 3.00 |
| Acacia | 0.53 |
| Glycerin | 5.00 |
| Boric acid | 3.00 |
| Ricinoleic acid | 0.75 |
| p-hydroxybenzoic acid, propyl ester | 0.05 |
| Purified water qs ad | 100.0 |

The tragacanth and acacia are intermixed thoroughly with the glycerin; ricinoleic acid and active ingredient are then added to the mixture. The p-hydroxybenzoate and boric acid are dissolved in water (with heating if necessary), and the solution is added to the prior mixture, with stirring and warming to dissolve. The mixture becomes gelatinous upon cooling.

For each application approximately 1 gram of the gel is vaginally administered to an adult human female with a suitable syringe.

(c) Vaginal suppository

| Ingredients | % w/w |
|---|---|
| Active ingredient | 1.0 |
| Polyethylene glycol 4000 | 20.0 |
| Butylated hydroxyanisole | 0.01 |
| Polyethylene glycol 1000 qs ad | 100.0 |

The polyethylene glycol solids are mixed and heated to 70°–80°, and the BHA dissolved in the mixture. After cooling to 45° C., the active ingredient is suspended in the above mixture by stirring. The suspension is poured into molds which are of sufficient size to form suppositories of about 3 gm each, and cooled.

(d) Effervescent vaginal tablets

| Ingredients | % w/w |
|---|---|
| Active ingredient | 1.0 |
| Anhydrous citric acid | 35.0 |
| Sodium bicarbonate | 15.0 |
| Polyethylene glycol 6000 | 20.0 |
| Lactose qs ad | 100.0 |

The above ingredients are combined and granulated using methanol as the solvent. The formulation is then dried and formed into tablets containing 20 mg of active compound with an appropriate tableting machine.

(e) Vaginal spray-foam

| Ingredients | % w/w |
|---|---|
| Active ingredient | 2.0 |
| Emulsion base | 90.0 |
| Propellant 12/114 (40:60) | 8.0 |

The emulsion base is made up according to the following % w/w composition:

| | |
|---|---|
| myristic acid | 1.33 |
| stearic acid | 5.33 |
| cetyl alcohol | 0.50 |
| lanolin | 0.20 |
| isopropyl myristate | 1.33 |
| triethanolamine | 3.33 |
| glycerin | 4.70 |
| polyvinylpyrrolidine | 0.34 |
| purified water | 82.93 |

The ingredients of the emulsion base, except for the water, are mixed in a stainless steel container kept at 70°–80°. 80% of the water to be used is also heated to 70°–80° and mixed during heating with a homomixer at moderate speed. After complete addition, the speed of mixing is increased for several minutes. The mixture is then cooled to room temperature and a solution containing the active ingredient in the remaining 20% water is added with continuous mixing. The preparation is placed in an appropriate spray can, topped with the propellant mixture, and sealed.

For each application approximately 0.5 gm of the foam are vaginally administered.

(f) Vaginal soluble waffle

| Ingredients | % w/w |
|---|---|
| Active ingredient | 1.0 |
| Starch | 10.0 |
| Water soluble lanolin qs ad | 100.0 |

The above ingredients are thoroughly mixed and pressed into 0.8 gm waffles with a suitable press.

EXAMPLE 6

The following pharmaceutical compositions are representative of those which may be used for oral administration to a male mammal for contraceptive use. The active ingredient illustrated is the same as for that in Example 5 although any active ingredient referred to above may be utilized.

(a) Oral formulation tablet

| Ingredients | Parts by Weight |
|---|---|
| Active ingredient | 200 |
| Magnesium stearate | 3 |
| Starch | 30 |
| Lactose | 116 |
| Polyvinylpyrrolidone | 3 |

The above ingredients are combined and granulated using methanol as the solvent. The formulation is then dried and formed into tablets containing 200 milligrams of active compound with an appropriate tableting machine.

(b) Implant formulation

| Ingredients | % w/w |
|---|---|
| Active ingredient | 2.0 |
| Polyethylene glycol 6000 | 5.0 |
| Cholesterol qs ad | 100.0 |

The ingredients are mixed and compressed into pellets of approximately 2 mm (diameter)×8 mm.

What is claimed is:

1. A compound of the formula

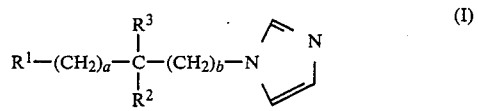

wherein:
R¹ is cycloalkyl of five to seven carbon atoms optionally substituted by one or more lower alkyl groups;
R² is cycloalkyl of five to seven carbon atoms, or cycloalkylalkyl of six to ten carbon atoms wherein when a cycloalkyl is cyclohexyl, it is optionally substituted by one or more lower alkyl groups;
R³ is hydrogen or methyl;
a is 0, 1, 2 or 3; and
b is 1, 2 or 3, or a pharmaceutically acceptable acid addition salt thereof.

2. A compound of claim 1 which is 1-[2,3-dicyclohexyl-n-propyl]imidazole or a pharmaceutically acceptable acid addition salt thereof.

3. A compound of claim 1 which is 1-[2-cyclohexylmethyl-3-cyclohexyl-n-propyl]imidazole or a pharmaceutically acceptable acid addition salt thereof.

4. A compound of claim 1 which is 1-[2-cyclopentylmethyl-3-cyclopentyl-n-propyl]imidazole or a pharmaceutically acceptable acid addition salt thereof.

5. A compound of claim 1 which is 1-[2-cycloheptylmethyl-3-cycloheptyl-n-propyl]imidazole or a pharmaceutically acceptable acid addition salt thereof.

6. A method of contraception in a female mammal comprising administering intravaginally, to a subject, prior to coitus, a spermotostatically or spermicidally effective amount of a compound of the formula

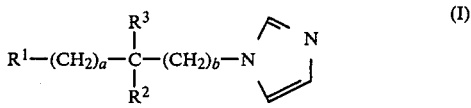

wherein:

$R^1$ is cycloalkyl of five to seven carbon atoms optionally substituted with one or more lower alkyl groups;

$R^2$ is alkyl of two to twelve carbon atoms, cycloalkyl of five to seven carbon atoms, or cycloalkylalkyl of six to ten carbon atoms wherein the cycloalkyl group is optionally substituted with one or more lower alkyl groups;

$R^3$ is hydrogen or lower alkyl;

a is 0, 1, 2 or 3; and b is 1, 2 or 3, or a pharmaceutically acceptable acid addition salt thereof.

7. A method of contraception in a male mammal, comprising administering orally to a subject in need of or desiring such effect, a spermicidally effective amount of the compound of claim 1 or a pharmaceutically acceptable acid addition salt thereof.

* * * * *